United States Patent [19]

Schwartz et al.

[11] Patent Number: 5,608,135
[45] Date of Patent: Mar. 4, 1997

[54] PROCESS FOR DECREASING CHLORINE CONTENT OF CHLORINATED HYDROCARBONS

[75] Inventors: Jeffrey Schwartz; Yumin Liu, both of Princeton, N.J.

[73] Assignee: The Trustees of Princeton University, Princeton, N.J.

[21] Appl. No.: 211,983
[22] PCT Filed: Apr. 14, 1993
[86] PCT No.: PCT/US93/03529
§ 371 Date: Aug. 15, 1994
§ 102(e) Date: Aug. 15, 1994
[87] PCT Pub. No.: WO93/21117
PCT Pub. Date: Oct. 28, 1993

[51] Int. Cl.$^6$ .......................... C07C 25/18; C07C 25/00
[52] U.S. Cl. .......................................... 588/207; 588/206
[58] Field of Search .......................... 588/206, 207, 588/248; 208/262.5, 262.1; 423/DIG. 20, 462; 210/909

[56] References Cited

U.S. PATENT DOCUMENTS

| | | | |
|---|---|---|---|
| 4,188,346 | 2/1980 | Markley | 570/204 |
| 4,447,667 | 5/1984 | Parker et al. | 585/469 |
| 4,804,779 | 2/1989 | Novinson | 562/542 |
| 4,931,167 | 6/1990 | Wilwerding | 208/262.5 |
| 4,957,717 | 9/1990 | Imamura et al. | 423/240 |
| 5,004,551 | 4/1991 | Sublette | 210/763 |
| 5,035,784 | 7/1991 | Anderson et al. | 204/158.14 |
| 5,345,032 | 9/1994 | Marks et al. | 588/207 |

OTHER PUBLICATIONS

Bergbreiter et al., *J. Org. Chem.*, 54, 5138–5141 (1989).
Bosin et al., *Tetrahedron Letters*, 4699–4700 (1973).
Carfagna et al., *J. Mol. Cat.* 57 (1989) 23–28.
Dennis et al., *Bulletin of Environmental Contamination and Toxicology*, 22:6, pp. 750–753 (1979).
Hill et al., *Appl. Biochem. Biotechnol.* 20/21, pp. 233–243, (1989).
Kozlowski, *J. Chromatogr.*, 318 (1985) 211–219.
Loubinoux et al., *Tetrahedron Letters*, 3951–3954 (1977).
Meunier, *J. Organometal. Chem.* 204 (1981), 345–346.
Rolla, *J. Org. Chem.*, 46, 3909–3911 (1981).
Stojkovski et al., *J. Chem. Tech. Biotechnol* (1990), 51, 407–417.
Stojkovski et al., *J. Chem. Tech. Biotechnol.* (1991), 51, 419–431.
Tabaei et al., *Tetrahedron Letters*, 2727–2730 (1991).
Waid, "PCBs and the Environment", 1986, vol. II, 78, CRC Press, Boca Raton, Florida.

*Primary Examiner*—David A. Simmons
*Assistant Examiner*—Linda L. Gray
*Attorney, Agent, or Firm*—Mathews, Woodbridge & Collins

[57] ABSTRACT

The chlorine content in a chlorinated hydrocarbon in the presence or absence of air and moisture can be reduced by bringing the chlorinated hydrocarbon into contact with a dechlorination reagent which comprises (i) a complex of a substantially nontoxic metal having at least two oxidation states and (ii) a reducing agent which reductively returns the complex from its second oxidation step to its first oxidation stage. A representative embodiment involves bis-($\eta^5$-cyclopentadienyl)titanium dichloride and sodium tetrahydridoborate.

7 Claims, 5 Drawing Sheets

PROCESS FOR DECREASING CHLORINE CONTENT OF CHLORINATED HYDROCARBONS

BACKGROUND OF THE INVENTION

1. Field of the Invention

This invention pertains to a process for decreasing the content of chlorine in chlorinated hydrocarbons.

2. Description of the Related Art

Various chlorinated hydrocarbons such as polychlorinated biphenyls, tetrachloroethylene, trichloroethylene, 1,2,3-trichloropropane, polychlorinated naphthalene, chlorine containing fluorocarbons ("Freons"), polychlorinated cyclodienes such as aldrin and dieldrin, polychlorinated bicycloalkanes such as mirex etc., are recognized environmental contaminants. Numerous chemical, physical, and microbiological methods for eliminating these presently are under investigation. While microbiological techniques are useful in bioremediation of many contaminants, such techniques have not proven satisfactory for highly chlorinated products such as those containing four or more chlorine atoms; see e.g., Hill et al., *Appl. Biochem. Biotechnol.*, 20/21, 233 (1989) and Waid, "PCBs and the Environment," Vol. II, 78, CRC Press, Boca Raton, Fla.

Various chemical approaches have been investigated but again it appears the greater the number of chlorine atoms in a target contaminant, the more difficult the dechlorination. Moreover systems which appear to be useful in the controlled environment of the laboratory encounter unexpected difficulties when an attempt is made to adapt the system to the competitive and ambient environment where such highly chlorinated products pose the greatest problem.

Wilwerding, U.S. Pat. No. 4,931,167, describes the degradation of polychlorinated biphenyls in a non-aqueous medium using anhydrous metal halides such as the chlorides and bromides of aluminum, titanium, tin, iron, etc.

Imamura et al., U.S. Pat. No. 4,957,717, describe the disposal of organic compounds by burning them in contact with a catalyst of a composite oxides such as titanium-silicon composite oxides and titanium-silicon-zirconium composite oxides.

Anderson et al., U.S. Pat. No. 5,035,784, describe degradation of polychlorinated biphenyls by photocatalysis by ultraviolet light utilizing porous titanium ceramic membranes.

Meunier, J. *Organometal. Chem*, 204 (1981), 345–346 describes the selective reduction of aromatic iodides with sodium borohydride activated by a catalytic amount of bis-($\eta^5$-cyclopentadienyl)titanium dichloride or $\eta^5$-cyclopentadienyltitanium trichloride in dimethylformamide and in the presence of air. Aromatic chlorine atoms were not affected.

Kozloski, J. *Chromatogr.*, 318 (1985) 211–219 describes partial catalytic dechlorination of polychlorinated biphenyls with sodium borohydride and nickel boride catalyst.

Stojkovski et al., *J. Chem. Tech. Biotechnol.* 1990. 51, 407–417, describe dechlorination of polychlorinated biphenyls and polychlorinated naphthalenes with nickel chloride/sodium borohydride catalysts. In a companion paper, *J. Chem. Tech. Biotechnol.*, 1991, 51, 419–431, Stojkovski et al. extend the use of this nickel chloride/sodium borohydride system to chlorinated cyclodiene and bicyclic insecticides.

Bosin et al., *Tetrahedron Letters*, 4699–4650 (1973) report on the reduction of aryl halides with a sodium borohydride-palladium system.

Carfagna et al., *J. Mol. Cat.* 57 (1989) 23–28, describe the use of magnesium hydride and various metal halides in the reduction of aryl monohalides.

Rolla, *J. Org. Chem.*, 46, 3909–3911 (1981) reports on the use of sodium borohydride to reduce a variety of halogenated hydrocarbons using hexadecyltributylphosphonium bromide as a catalyst.

Bergbreiter et al., *J. Org. Chem.*, 54, 5138–5141 (1989) describe the use of tin catalyst attached to soluble polyethylene and polystyrene for use in alkyl halide reductions.

Loubinoux et al., *Tetrahedron Letters*, 3951–3954 (1977) report on the activation of sodium hydride by certain metal salts in the reduction of various organic halides.

Tabaei et al., *Tetrahedron Letters*, 2727–2730 (1991) describe the use of polyethylene glycol or tetraethylene glycol in the metal catalyzed reduction of chlorinated hydrocarbons with sodium borohydride or sodium alkoxyborohydride.

SUMMARY OF THE INVENTION

The present invention involves a method for chemically reducing the overall chlorine content in chlorinated compounds, generally but not necessarily chlorinated hydrocarbons. The process is characterized by the ability to operate economically in a mixed ambient environment, notably in the presence of water and oxygen found in air. Although not so limited, it has particular value as a pretreatment to microbiological degradation of chlorinated hydrocarbons in that highly chlorinated compounds which are resistant to bioremediation can be converted to compounds having a lower content of chlorine, thereby being more susceptible to microbiological degradation.

Figure 1:
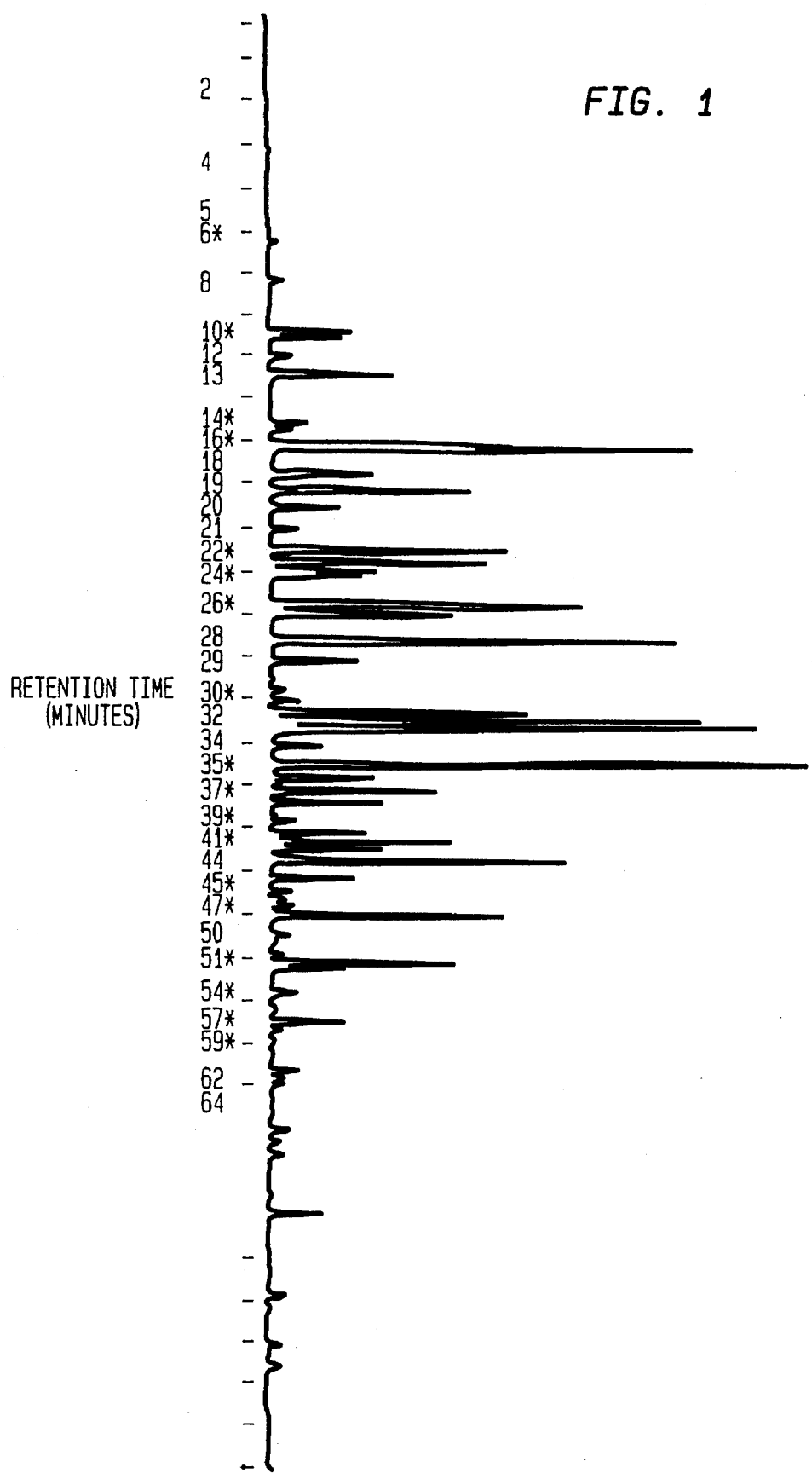
FIG. 1 shows a gas chromatogram of Samples I and II before treatment.

Broadly the process involves bringing the chlorinated hydrocarbon into contact with a dechlorination reagent of the type described herein. Heat can be applied to accelerate the reaction. The dechlorination reagent contains two principal components.

The first component of the dechlorination reagent is a metal complex having at least two oxidation states. In a first, lower oxidation state, the complex is operable to transfer an electron to the chlorinated hydrocarbon and thereby reductively eliminate a chlorine atom from the chlorinated hydrocarbon. In transferring the electron, the complex assumes its second, higher oxidation state; i.e., it is oxidized.

The second component of the reagent is a reducing agent operable to reductively return the complex from its second oxidation step to its first oxidation stage; i.e., to reduce the complex back to its original oxidation state.

It will be appreciated that the net result of these two reactions is the consumption of the second component and the regeneration of the first component. Consequently the first component effectively acts as a catalyst in the sense that while it participates in the reduction of chlorinated hydrocarbon, it is returned to its original oxidation state in which it can enter into a further reaction. Consequently the amount of the first component which must be introduced into the environment is relatively small.

Moreover while these two components are referred to herein as a reagent or system in that they co-act, in use they can be introduced either in pre-formed combination or separately. The hydridoborate can added all at once or in portions during the course of the reaction, the latter procedure often producing a higher efficiency of dechlorination.

It is critical to the process, however, that both components operate under the ambient conditions of the environment and do so without causing further contamination. For example, complexes containing nickel may be technically effective as the first component in reducing chlorinated hydrocarbon but are unsuitable because the nickel of the complex thus introduced into the environment itself is toxic. Similarly sodium hydride and lithium aluminum hydride in theory are effective as the second component but both react with water and thus are unsuitable, being unstable in a mixed environment.

The first component will contain a substantially nontoxic transition metal of Group 4 or 5 (IVa or Va) and will form a complex with multidentate and unidentate organic and inorganic ligands. Particularly preferred are titanium and zirconium compounds including benzoates, chlorides, salen complexes, prophyrins, tris(pyrazoyl) borates, poly(alkylamino) complexes, poly(alkylamino) chelates, poly(thioalkyl) complexes, poly(thioalkyl) chelates, and mixtures thereof. One highly effective subclass are the organometallic complexes of titanium and zirconium such as bis-($\eta^5$-cyclopentadienyl)titanium dichloride, bis-($\eta^5$-cyclopentadienyl)zirconium dichloride, $\eta^5$-cyclopentadienylzirconium trichloride, and $\eta^5$-cyclopentadienyltitanium trichloride. Particularly useful in view of its currently relatively low cost and performance is bis-($\eta^5$-cyclopentadienyl)titanium dichloride, also known as titanocene dichloride.

The second component will be a hydridoborate, typically a polyhydridoborate, such as an alkali metal or ammonium salt of a tetrahydridoborate, thiocyanatotrihydridoborate, cyanotrihydridoborate, acyloxytrihydridoborate, octahydridotrihydridoborate, trialkylhydridoborate, acetanilidotrihydridoborate, trialkoxyhydridoborate, and metal chelates thereof. Particularly useful in view of its current relatively low cost and performance is sodium tetrahydridoborate.

In the absence of the first component, the hydridoborate may show some dechlorination properties but the rate is far slower and the range of chlorinated compounds in which such dechlorination is seen is far more limited than when the metal complex is present.

The target polychlorinated hydrocarbons, particularly polychlorinated aromatic compounds, often present a complex mixture of cogeners. In the case of PCB's for example, the cogeners present can number in the hundreds. It thus is convenient to study the use of the present reagent with substantially pure chlorinated compounds. As shown below, the usefulness of the reagent in reducing the chlorine content of pure compounds also is seen in mixtures of chlorinated compounds.

The halogenated hydrocarbons on which the process is operable include halogenated aromatic, aliphatic, and olefinic compounds such as polychlorinated biphenyls (PCB's), tetrachloroethylene, trichloroethylene, 1,2,3-trichloropropane, and the like. Other functional groups such as oxo groups (ketones, carboxylic acids and esters), amino groups (including secondary and tertiary amino groups), nitro groups and the like also can be present in the compound or compounds being treated. Such groups, if susceptible to reduction, may be reduced in the course of the process. Such products generally are equally or more amenable to bioremediation.

It will be appreciated that upon removal of one chlorine atom from a given polychlorinated compound, a further chlorine atom can and will be removed from the product by repetition of the reaction and in fact typically starting with a highly chlorinated compound a series of different products, each having a fewer but different number of chlorine atoms per molecule, will be produced. For example, beginning with hexachlorobenzene, the first product will be pentachlorobenzene. The pentachlorobenzene thus formed in turn will be converted to 1,2,3,4-tetrachlorobenzene and 1,2,4,5-tetrachlorobenzene. 1,2,4,5-Tetrachlorobenzene produces 1,2,4-trichlorobenzene. Since these reactions proceed concurrently, a plurality of products generally are formed but the net result of the process will be a reduction in the overall chlorine content of the chlorinated hydrocarbon.

The reactive intermediate generated from the chlorinated hydrocarbon can react with other organic materials present in the rection area. For example if the treatment of 1,2,4,5-tetrachlorobenzene is conducted in the presence of dimethylformamide as a solvent, the products can include not only 1,2,4-trichlorobenzene but also N,N-dimethyl-2,4,5-trichloroaniline. Similarly, when the process is conducted with 1,3,5-trichlorobenzene, both N,N-dimethyl-3,5-dichloroaniline and 1,3-dichlorobenzene will be produced. Whether this involves a nucleophilic mechanism or free radical mechanism is not known but the products so formed are in any event more amenable to bioremediation by reason of the net reduction in the number of chlorine atoms.

Moreover, the present reagent appears to operate effectively not only on highly chlorinated compounds and but also on compounds containing only a few chlorine atoms.

The following examples will serve to further exemplify the present invention without being construed as being a limitation thereof. The designations used herein for the metal complexes used are as follows:

| Metallic Complex | Designation |
| --- | --- |
| oxo(tetraphenylporphyrinato)titanium oxide | A |
| $\eta^5$-cyclopentadienyltitanium trichloride | B |
| (salen)titanium dichloride | C |
| titanium trichloride | D |
| bis($\eta^5$-cyclopentadienyl)titanium dichloride | E |
| titanium tetrapropoxide | F |
| oxobis(acetylacetonato)titanium | G |
| titanium boride | H |
| {tris[3,5-dimethylpyrazolyl]borate} titanium trichloride | I |
| bis($\eta^5$-cyclopentadienyl)zirconium dichloride | J |

EXAMPLE 1

A. Without Catalyst

A mixture of 2 mmol of hexachlorobenzene and 8 mmol of sodium tetrahydridoborate in 10 mL of dimethylformamide was heated with stirring for 36 hours at 88° C. in an air atmosphere in a reaction vessel equipped with a condenser. At the end of this time, water was added and the mixture extracted with ether. Analysis of the ethereal extract by gas chromatography (flame ionization detector) and by gas chromatography/mass spectrography indicated the following composition:

| Compound | mmol |
| --- | --- |
| tetrachlorobenzenes | 0.475 |
| N,N-dimethyltetrachloroanilines | 0.482 |
| N,N-dimethyltrichloroanilines | 0.363 |
| trichlorobenzenes | 0.107 |

B. With Catalyst

By following substantially the same procedure as that set forth in Part A with 1.87 mmol of hexachlorobenzene and 7.88 mmol of sodium tetrahydridoborate in 10 mL of dimethylformamide with heating at 85° C. but adding 0.19 mmol of metal complex I, the following reaction composition was obtained after 11 hours.

| Compound | mmol |
| --- | --- |
| tetrachlorobenzenes | 0.502 |
| N,N-dimethyltetrachloroanilines | 0.682 |
| N,N-dimethyltrichloroanilines | 0.393 |
| trichlorobenzenes | 0.069 |

EXAMPLE 2

Following the procedure of Example 1, Part B, 2 mmol of hexachlorobenzene, 8 mmol of sodium tetrahydridoborate, and 0.2 mmol of each of metal complexes A, B, C, D, and E were heated in 10 mL of dimethylformamide.

The conditions and results are summarized on Table I.

B. With Catalyst

By following substantially the same procedure as that set forth in Part A but adding 0.2 mmol of metal complex E, the following reaction composition was obtained after 1.1 hours.

| Compound | mmol |
| --- | --- |
| pentachlorobenzene (starting compound) | 0.732 |
| 1,2,4,5-tetrachlorobenzene | 0.566 |
| 1,2,3,4-tetrachlorobenzene | 0.077 |
| 1,2,4-trichlorobenzenes | 0.013 |

EXAMPLE 4

A. Without Catalyst

A mixture of 1 mmol of 1,2,4,5-tetrachlorobenzene and 4 mmol of sodium tetrahydridoborate in 10 mL of dimethylformamide was heated with stirring for 3.5 hours at 95° C. in an air atmosphere in a reaction vessel equipped with a condenser. The reaction mixture, extracted and analyzed as described above, had the following composition:

| Compound | mmol |
| --- | --- |
| 1,2,4,5-tetrachlorobenzene (starting compound) | 0.84 |
| 1,2,4-trichlorobenzene | 0.11 |
| N,N-dimethyl-2,4,5-trichloroaniline | 0.05 |

B. With Catalyst

By following substantially the same procedure as that set forth in Part A but adding 0.2 mmol of metal complex E, the following reaction composition was obtained after 3.5

TABLE I

| Complex | Temp. °C. | Time Hours | $C_6Cl_3H_3$ mmol | $C_6Cl_4H_2$ mmol | $C_6Cl_3H_2N(CH_3)_2$ mmol | $C_6Cl_4HN(CH_3)_2$ mmol | $C_6Cl_3H_2OH$ mmol | $C_6Cl_5H$ mmol |
| --- | --- | --- | --- | --- | --- | --- | --- | --- |
| A | 80 | 18 | 0.045 | 0.929 | 0 | 0.033 | 0.150 | 0.182 |
| B | 79 | 18 | 0.048 | 1.033 | 0 | 0.109 | 0 | 0.308 |
| C | 70 | 18 | 0.019 | 0.558 | 0.047 | 0.528 | 0 | 0.179 |
| D | 84 | 18 | 0.081 | 0.819 | 0.143 | 0.416 | 0 | 0.174 |
| E | 72 | 18 | 0.018 | 0.740 | 0 | 0.018 | 0.024 | 0.177 |
| None | 72 | 36 | 0.107 | 0.475 | 0.363 | 0.482 | 0 | 0 |

EXAMPLE 3

A. Without Catalyst

A mixture of 2 mmol of pentachlorobenzene and 8 mmol of sodium tetrahydridoborate in 10 mL of dimethylformamide was heated with stirring for 1.1 hours at 85° C. in an air atmosphere in a reaction vessel equipped with a condenser. At the end of this time, water was added and the mixture extracted with ether. Analysis of the ethereal extract by gas chromatography (flame ionization detector) and by gas chromatography/mass spectrography indicated the following composition:

| Compound | mmol |
| --- | --- |
| pentachlorobenzene (starting compound) | 1.086 |
| 1,2,4,5-tetrachlorobenzene | 0.56 |
| 1,2,3,4-tetrachlorobenzene | 0.063 |

| Compound | mmol |
| --- | --- |
| 1,2,4,5-tetrachlorobenzene (starting compound) | 0.12 |
| trichlorobenzene | 0.45 |
| N,N-dimethyl-2,4,5-trichloroaniline | 0.43 |

EXAMPLE 5

Following the procedure of Example 4, Part B, 1 mmol of 1,2,4,5-tetrachlorobenzene, 4 mmol of sodium tetrahydridoborate, and the indicated amount of each of metal complexes E, E, F, and J were heated in dimethylformamide.

The conditions and results are summarized on Table II.

TABLE II

| Complex | Temp. °C. | Time hours | Metal Complex mmol | $C_6Cl_3H_3$[a] mmol | $C_6Cl_3H_2N(CH_3)_2$[b] mmol | $C_6Cl_4H_2$ (Recovered) mmol |
|---|---|---|---|---|---|---|
| E | 95 | 3.5 | 0.1 | 0.45 | 0.43 | 0.12 |
| E | 95 | 1.8 | 0.2 | 0.42 | 0.42 | 0.16 |
| F | 95 | 3.5 | 0.1 | 0.33 | 0.38 | 0.29 |
| J | 95 | 1.8 | 0.1 | 0.30 | 0.56 | 0.14 |
| — | 95 | 3.5 | — | 0.11 | 0.05 | 0.84 |

[a] = 1,2,4-trichlorobenzene
[b] = N,N-dimethyl-2,4,5-trichloroaniline

EXAMPLE 6

Following the procedure of Example 4, Part B, 2 mmol of 1,2,4,5-tetrachlorobenzene, 8 mmol of sodium tetrahydridoborate, and the indicated amount of each of metal complexes A, B, D, C, and I were heated in dimethylformamide.

The conditions and results are summarized on Table III.

TABLE III

| Complex | Temp. °C. | Time hours | Metal Complex mmol | $C_6Cl_3H_3$[a] mmol | $C_6Cl_3H_2N(CH_3)_2$[b] mmol | $C_6Cl_4H_2$ (Recovered) mmol |
|---|---|---|---|---|---|---|
| A | 75 | 5.8 | 0.2 | 0.06 | 0.06 | 1.88 |
| B | 75 | 5.8 | 0.2 | 0.56 | 1.24 | 0.20 |
| C | 75 | 5.8 | 0.2 | 0.48 | 1.26 | 0.26 |
| D | 75 | 5.8 | 0.2 | 0.48 | 1.36 | 0.16 |
| I | 75 | 5.8 | 0.2 | 0.48 | 1.30 | 0.22 |

[a] = 1,2,4-trichlorobenzene
[b] = N,N-dimethyl-2,4,5-trichloroaniline

EXAMPLE 7

A. Without Catalyst

A mixture of 8 mmol of sodium tetrahydridoborate and 2 mmol of 1,4-dichlorobenzene in 10 mL of dimethylformamide was heated with stirring for 6.5 hours at 80° C. in an air atmosphere in a reaction vessel equipped with a condenser. Upon extraction and analysis as described above, only starting material could be detected.

B. With Catalyst

By following substantially the same procedure as that set forth in Part A but adding 0.2 mmol of metal complex E, the following reaction composition was obtained after 6.5 hours.

| Compound | mmol |
|---|---|
| 1,4-dichlorobenzene (starting compound) | 1.96 |
| chlorobenzene | 0.04 |

EXAMPLE 8

1,2,3-Trichloropropane was treated with sodium tetrahydridoborate and metal complex E at 100° C. for 1 hour in substantially the fashion described above. Gas chromatography/mass spectrography indicated no 1,2,3-trichloropropane remained in the reaction mixture.

EXAMPLE 9

Treating tetrachloroethylene (325 mg) with sodium tetrahydridoborate and metal complex E at 93° C. for 3 hours and 20 min. in substantially the fashion described above converted 98% of starting material to trimethylamine, 1,1dichloroethylene, 1,2-dichloroethylene, and N,N-dimethylaminomethanol as determined by gas chromatography/mass spectrography.

EXAMPLE 10

Five and one-half parts by weight of a commercial mixture of polychlorinated biphenyls (Aroclor 1248) were extracted with ether and the ether then evaporated in vacuo. To the residue were added 45 parts by weight of sodium tetrahydridoborate, 25 parts by weight of metal complex E, and 1 part by volume of dimethylformamide. The mixture was heated at 92° C. After one hour the mixture became viscous and an additional 0.5 part by volume of dimethylformamide was added. After an additional 17 hours of heating (a total of 18 hours), the reaction products were extracted with ether and passed through a short column of silica gel to remove the residual metal complex. Upon analysis, the reaction product contained about 25% (1.36 parts by weight) of polychlorinated biphenyls, indicating a 75% reduction.

The results of utilization of the foregoing procedure with metal catalysts A, B, C, D, E, H, I, and J are shown on Table IV.

TABLE IV

| Complex | Amount mg | $NaBH^4$ mg | Temp. °C. | Time hours | PCB (Before) mg | PCB (After) mg | Dechlorination |
|---|---|---|---|---|---|---|---|
| A | 17.6 | 12.6 | 100 | 18 | 3.3 | 0.76 | 77% |
| B | 9.0 | 10.6 | 100 | 18 | 3.3 | 1.39 | 58% |

TABLE IV-continued

| Complex | Amount mg | NaBH⁴ mg | Temp. °C. | Time hours | PCB (Before) mg | PCB (After) mg | Dechlorination |
|---|---|---|---|---|---|---|---|
| C | 12.5 | 12.4 | 100 | 18 | 3.3 | 2.37 | 28% |
| D | 7.0 | 10.5 | 100 | 18 | 3.3 | 1.24 | 62% |
| E | 8.0 | 13.6 | 100 | 18 | 3.3 | 0.28 | 92% |
| H | 145.0 | 45.0 | 92 | 18 | 7.0 | 4.60 | 34% |
| I | 9.9 | 12.9 | 100 | 18 | 3.3 | 1.79 | 46% |
| J | 25.0 | 45.0 | 92 | 18 | 7.5 | 2.07 | 72% |

EXAMPLE 11

A commercial mixture of polychlorinated biphenyls (Aroclor 1248, 3.3 parts by weight) was extracted with ether and the ether then evaporated in vacuo. To the residue were added 21 parts by weight of bis($\eta^5$-cyclopentadienyl)titanium tetrahydridoborate and 1 part by volume of dimethylformamide. The mixture was heated at 100° C. After a total of 18 hours, the reaction products were extracted with ether and passed through a short column of silica gel to remove the residual metal complex. Upon analysis, the reaction product contained about 40% (1.31 parts by weight) of polychlorinated biphenyls, indicating a 60% dechlorination.

The foregoing example demonstrates that the metal complex and the hydridoborate can be combined in the same molecule to achieve the desired result, requiring however a stoichiometric amount of the reagent. Although this confirms the working premise of the invention, it introduces metal in excess of that which is required in order to effectively lower chlorine content with hydridoborate and a catalytic amount of the metal complex.

EXAMPLE 12

A mixture of 0.3 mmol of metal complex E and 30.0 mmol of sodium tetrahydridoborate in 30 mL of dimethylformamide was heated with stirring for 1 hour at 92° C. in an air atmosphere in a reaction vessel equipped with a condenser. The reaction product was filtered through a Celite plug and a fine glass frit to produce the dehalogenation reagent as a dark brown solution.

If 1,2,4,5-tetrachlorobenzene is added to this solution and the mixture then heating at 92° C., it is reduced to a level below 10% in about 60–65 minutes with the formation of 1,2,4-trichlorobenzene and N,N-dimethyl-2,4,5-trichloroaniline (as determined by gas chromatography/mass spectrography).

EXAMPLE 13

A reaction vessel equipped with a condenser is charged with approximately 5 g of soil contaminated with polychlorinated biphenyls. A portion of sodium tetrahydridoborate, and 150 mg of metal complex E in dimethylformamide are added and the mixture is heated with stirring at 100° C. in an air atmosphere in a reaction vessel. After 30 minutes, additional sodium tetrahydridoborate and metal complex E are added. (Any material on the walls of the vessel can be washed off with dimethylformamide.) After another 20 minutes, additional sodium tetrahydridoborate is added and the reaction mixture is stirred for 18 hours. The reaction can be quenched with water and the reaction mixture exhaustively extracted with ether (to insure partition of all chlorinated biphenyls). Analysis of the ethereal extracts is performed by gas chromatograph and compared against the untreated contaminated soils.

The results of utilization of the foregoing procedure with samples of soil contaminated with polychlorinated biphenyls produced are shown on Table V.

TABLE V

| Soil Sample | Weight g | NaBH₄ mg | PCB (Before) mg | PCB (After) mg | Dechlorination |
|---|---|---|---|---|---|
| I | 5.1 | 870 | 47.1 | 34.14 | ·28% |
| II | 5.0 | 930 | 47.1 | 30.00 | 36% |
| III | 5.1 | 880 | 1.33 | 0.88 | 34% |

Approximately 2 to 5 g of the soil sample are placed into a 20 mL serum vial, the sample is amended with an equal volume mL/g of distilled water and to this mixture are added 10 mL of diethyl ether. The vial is sealed and shaken on a rotary shaker for 24 hours. The ether phase then is transferred to a 1.5 mL serum vial for analysis. (If needed, the original ether extract can be either concentrated or diluted to ensure accurate sample analysis.)

Samples containing interfering substances are cleaned using appropriate methods. Non-PCB oils (hydraulic fluids, mineral oil, etc.) are removed by passing the extracts through a conditioned magnesium silicate matrix. The retained PCBs are eluted from the matrix with hexane and the wash is either diluted or concentrated for GC analysis. Samples which are found to contain elemental sulfur are cleaned by combining 2 mL of the sample extract with 1 mL of reagent containing 3.39 g of tetrabutylammonium hydrogen sulfate and 25 g sodium sulfite in 100 mL of water and 1 mL of 2-propanol. After mixing for five minutes, an additional 3 mL of water are added to remove the alcohol and reagent. The ethereal layer is transferred to a gas chromatograph equipped with an electron capture detector (300° C.), a split/splitless capillary injector (300° C.), and a fused silica column (length=30 m, inner diameter=0.25 mm) coated with a 0.25 μm bonded liquid phase of polydimethylsiloxane. The column is temperature programmed from 160° C. to 200° C. at 2° C./min/no hold time to 240° C. at 8° C./min and held for 10 minutes. The gas flow rates are set as follows: carrier gas (helium) at 23 cm/sec (067 mL/min); make-up gas (nitrogen) at 33 mL/min; and a split ratio of 16.

Chromatograms of the samples are integrated on a peak-by-peak basis and the area of each peak is normalized with respect to standard mixtures of known PCB composition.

Figure 1A:
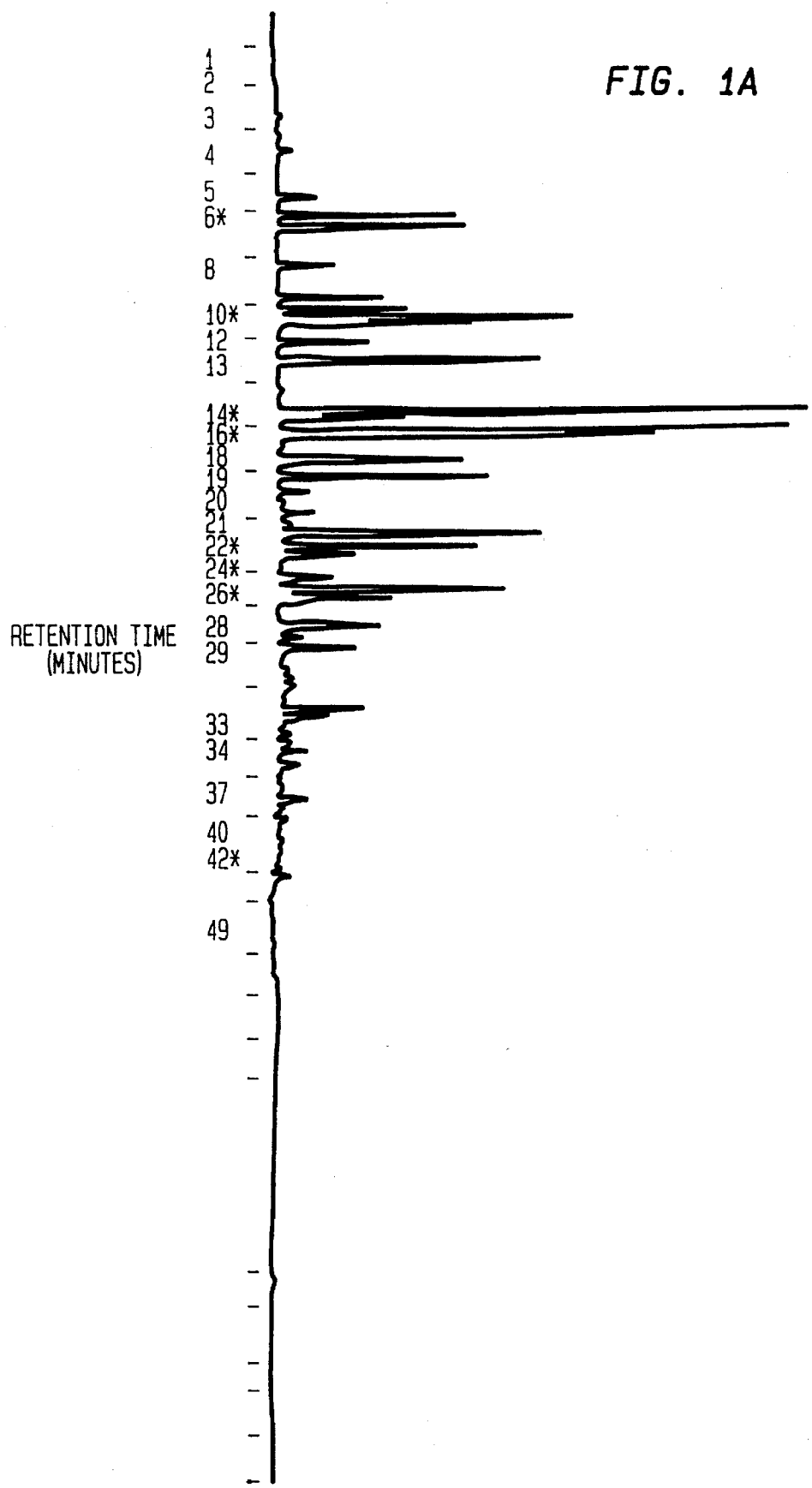
FIG. 1A shows a gas chromatogram of Sample I after treatment.
Figure 1B:
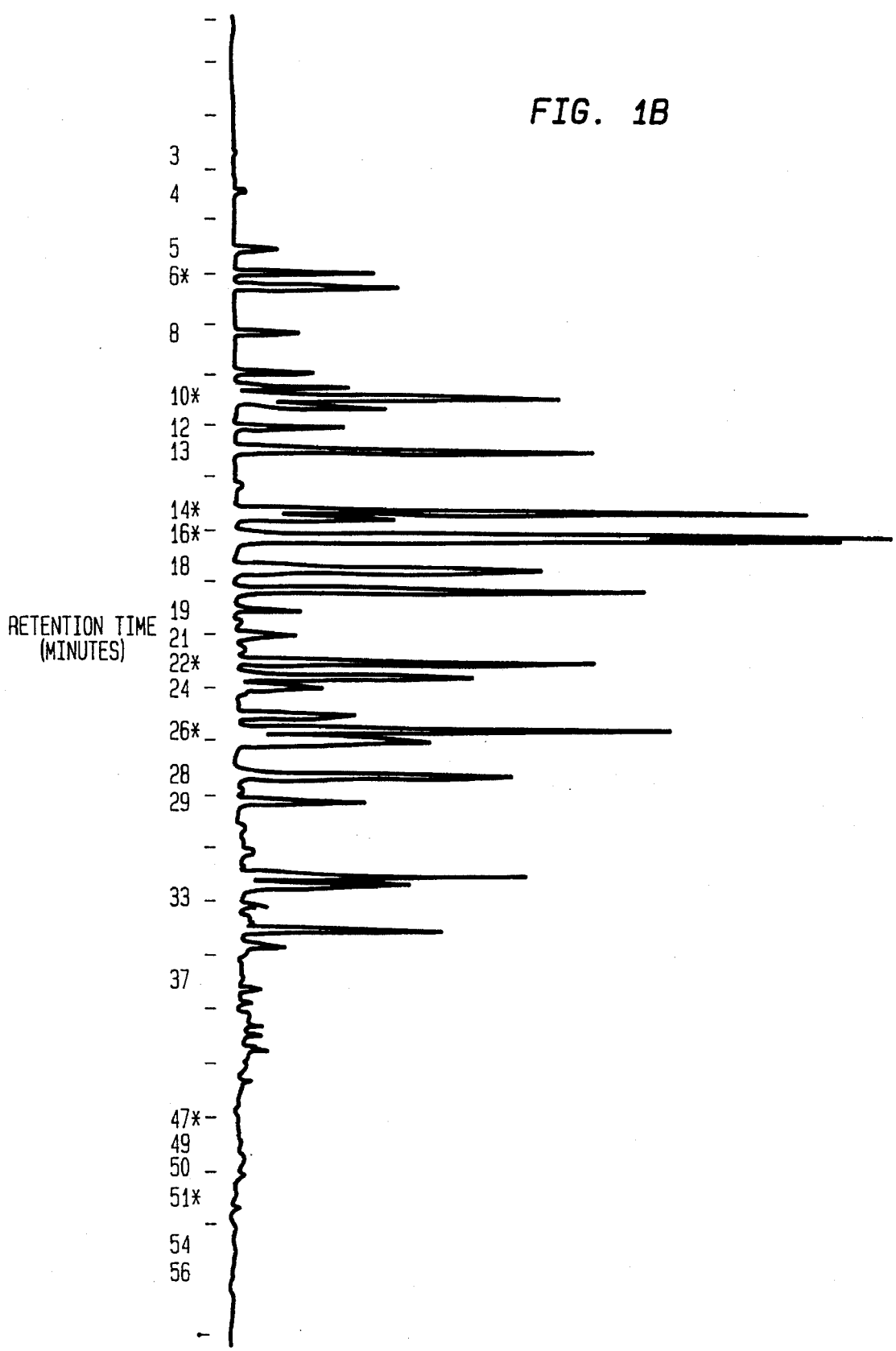
FIG. 1B shows a gas chromatogram of Sample II after treatment.

FIG. 1 is a gas chromatogram of soil before treatment from which Samples I and II were taken. The plotting attenuation is 40. The retention time is a function of the degree of chlorination. FIGS. 1A and 1B are gas chromatograms of Samples I and II, respectively, after dechlorination as described above. The plotting attenuation for FIG. 1A is 21; that for FIG. 1B is 31.

In addition to an overall decrease in chlorine content in both samples, it will be observed that the population of heavily chlorinated components (a retention time of about 30 minutes or more) has been greatly reduced, the heavily chlorinated products having been converted to more lightly chlorinated products.

Figure 2:
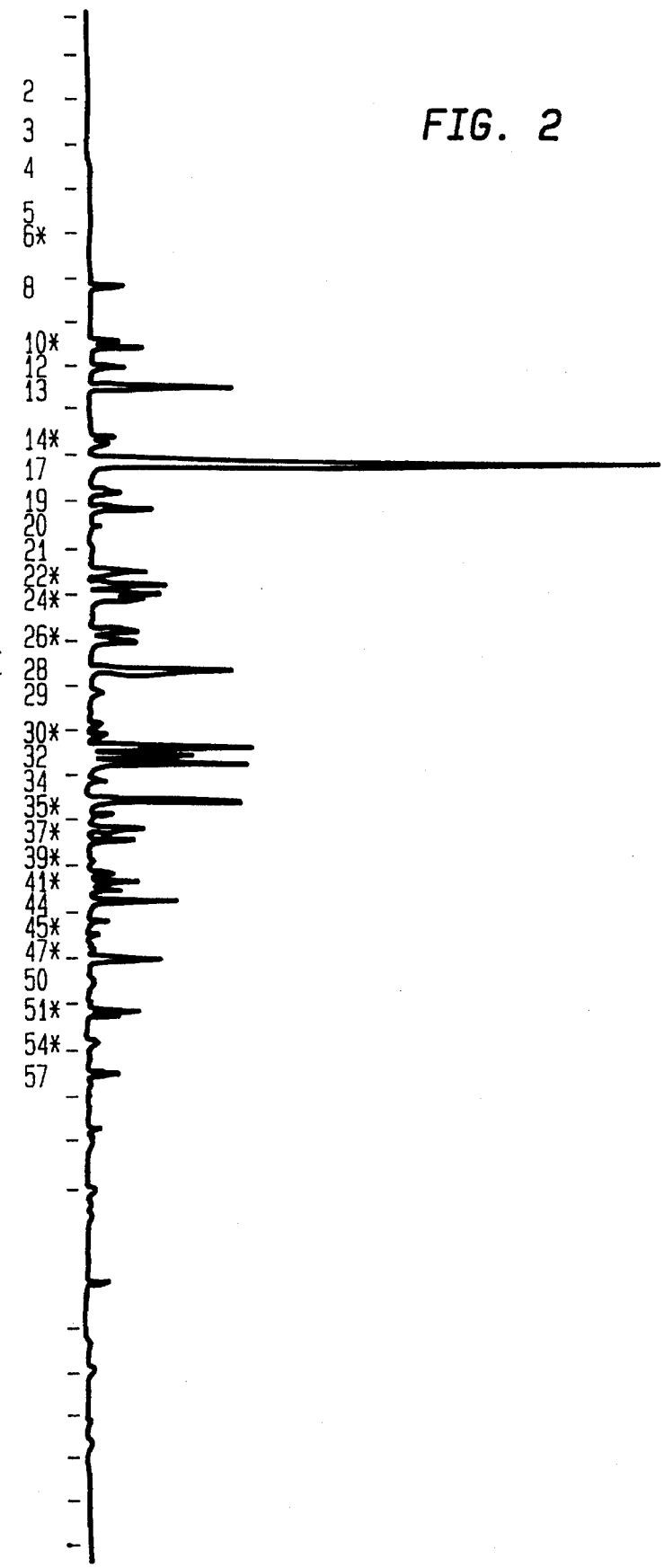
FIG. 2 shows a gas chromatogram of Sample III before treatment.
Figure 2A:
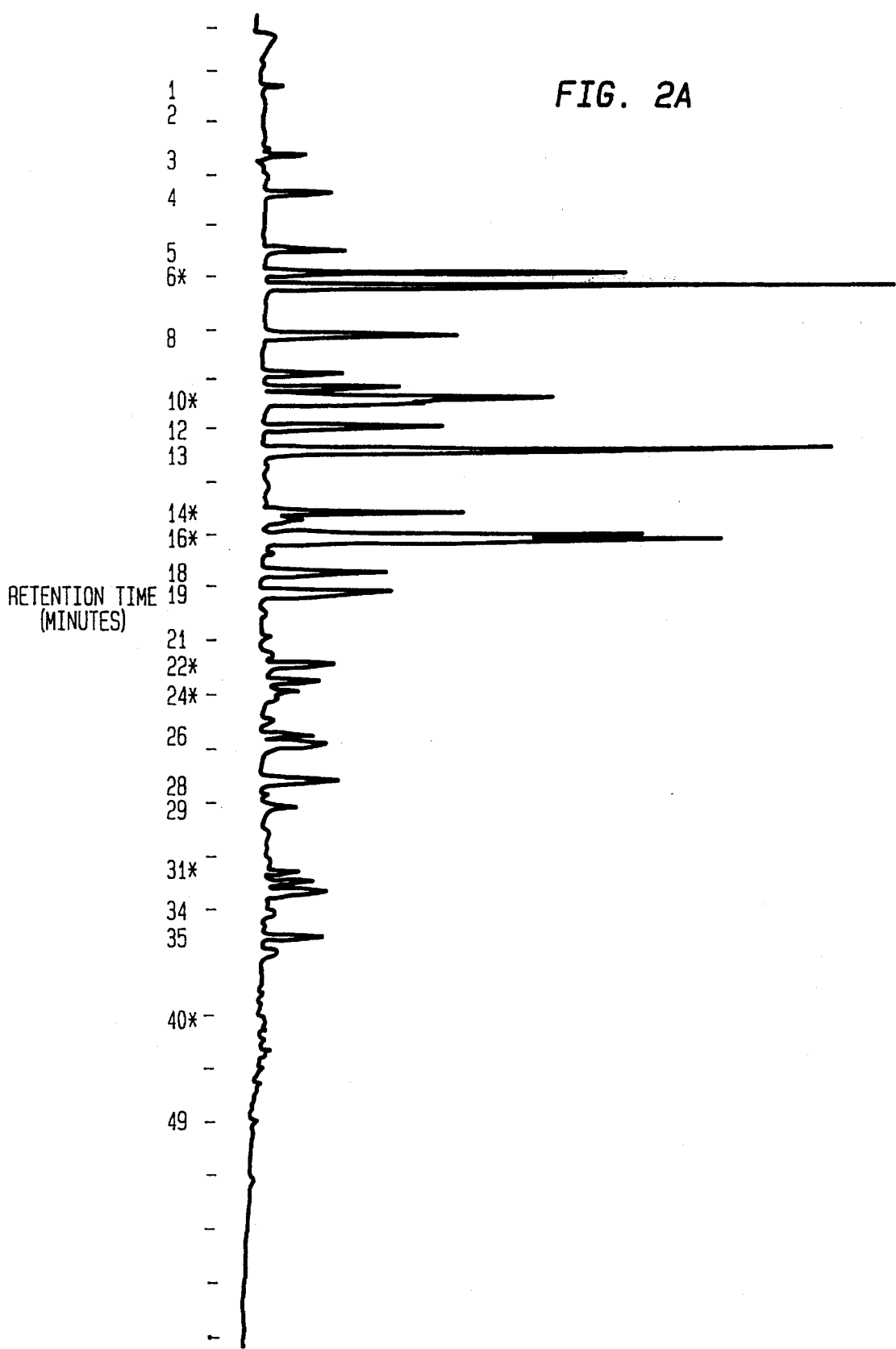
FIG. 2A shows a gas chromatogram of Sample III after treatment.

FIG. 2 is a gas chromatogram of Sample III before treatment. The plotting attenuation is 56. FIG. 2A is the chromatogram (plotting attenuation of 11) after dechlorination as described above. Again a shift in population from highly chlorinated compounds (retention time above about 30 minutes) to more lightly chlorinated compounds accompanies a reduction in overall chlorine content.

EXAMPLE 14

A flask equipped with a magnetic stir bar and a water cooled condenser with an oil bubbler was charged with sodium tetrahydridoborate (568 mg, 15.0 mmol), bis($\eta^5$-cyclopentadienyl)titanium dichloride (374 mg, 1.5 mmol), Aroclor 1248 (1095 mg, 3.75 mmol based on an average molecular formula: $C_{12}H_6Cl_4$), and N,N-dimethylacetamide (DMA; 15.0 ml). The flask was heated at 75° C. for 10 hours and at 105° C. for 4.25 hours. The reaction mixture was quenched with water (30 mL) and extracted with ethyl acetate (50 mL). The ethyl acetate solution was filtered through a short column of silica gel and washed with ethyl acetate. The resulting filtrate was analyzed by GC and compared with standard Aroclor 1248. Substantial reduction to mono-, di-, and trichloro PCBs was noted. No PCB containing more than three chlorine atoms per congener was present.

EXAMPLE 15

A flask equipped with a magnetic stir bar and a water cooled condenser with an oil bubbler was charged with 1,2,4,5-tetrachlorobenzene (648 mg, 3.0 mmol), sodium tetrahydridoborate (1135 mg, 30.0 mmol), bis($\eta^5$-cyclopentadienyl)titanium dichloride (75 mg, 0.3 mmol) and 1-methyl-2pyrrolidine (NMP; 30.0 ml). The reaction mixture was heated at 96° C. in an oil bath. After 4.25 hours, lithium chloride (1.09 g, 30.0 mmol) was added. Aliquots were withdrawn by syringe, quenched with water, and extracted with diethyl ether. The ether layer was analyzed with the results shown in the following table. Only trichlorobenzene was produced.

|   | TIME (min) | $C_6Cl_4H_2$ | $C_6Cl_3H_3$ |
|---|---|---|---|
| 1 | 34.0 | 0.924 | 0.076 |
| 2 | 84.0 | 0.829 | 0.171 |
| 3 | 218.0 | 0.642 | 0.358 |
| 4* | 254.0 | 0.605 | 0.395 |
| 5 | 279.0 | 0.517 | 0.483 |
| 6 | 331.0 | 0.355 | 0.645 |
| 7 | 402.0 | 0.248 | 0.752 |

*lithium chloride added

EXAMPLE 16

A flask equipped with a magnetic stir bar and a water cooled condenser with an oil bubbler was charged with 1,2,4,5-tetrachlorobenzene (648 mg, 3.0 mmol), sodium tetrahydridoborate (1135 mg, 30.0 mmol), bis($\eta^5$-cyclopentadienyl) titanium dichloride (75 mg, 0.3 mmol) and dimethylsulfoxide (30.0 ml). The reaction mixture was heated at 92° C. in an oil bath. Aliquots were withdrawn by syringe, quenched with water, and extracted with diethyl ether. The ether layer was analyzed with the results shown in the following table. Only trichlorobenzene was produced.

|   | TIME (min) | $C_6Cl_3H_3$ | $C_6Cl_4H_2$ | $\ln(C_6Cl_4H_2)$ |
|---|---|---|---|---|
| 1 | 85.000 | 0.069 | 0.931 | −0.071 |
| 2 | 180.000 | 0.128 | 0.872 | −0.137 |
| 3 | 285.000 | 0.174 | 0.826 | −0.191 |
| 4 | 340.000 | 0.205 | 0.795 | −0.229 |
| 5 | 426.000 | 0.246 | 0.754 | −0.282 |

EXAMPLE 17

A flask with a magnetic stir bar and a water cooled condenser with an oil bubbler was charged with 1,2,4,5tetrachlorobenzene (648 mg, 3.0 mmol), sodium tetrahydridoborate (1135 mg, 30.0 mmol), bis($\eta^5$-cyclopentadienyl)titanium dichloride (75 mg, 0.3 mmol), and N,N-dimethylacetamide (30.0 ml). The reaction mixture was heated at 95° C. in an oil bath. Aliquots were withdrawn by syringe, quenched with water, and extracted with diethyl ether. The ether layer was analyzed with the results shown in the following table. Only trichlorobenzene was produced an <1% of N, N-dimethyl-2,4,5-trichloroaniline were detected.

|   | TIME (min) | $C_6Cl_4H_2$ | $\ln(C_6Cl_4H_2)$ |
|---|---|---|---|
| 1 | 42.000 | 0.930 | −0.073 |
| 2 | 186.000 | 0.770 | −0.261 |
| 3 | 242.000 | 0.760 | −0.274 |
| 4 | 360.000 | 0.640 | −0.446 |
| 5 | 420.000 | 0.540 | −0.616 |

EXAMPLE 18

The formation of gas (mostly trimethylamine) in the chemical dechlorination process competes with the reaction between the reagent and the targeted chlorinated hydrocarbons. In order to maximize the reaction of the reagent with the chlorinated hydrocarbons, and to minimize the formation of gas, a sequential addition procedure can be used to maintain relatively low concentrations of sodium tetrahydridoborate in the system.

A reaction vessel was charged with chlorinated hydrocarbons (Aroclor 1248), a magnetic stir bar, sodium tetrahydridoborate (0.5 g), bis($\eta^5$-cyclopentadienyl)titanium dichloride (80 mg) and N,N-dimethylformamide (30.0 ml). The bottle was isolated by an oil bubbler and was heated to 95° C. After 1.5 hours, additional sodium tetrahydridoborate (0.5 g) was added. Gas evolution was observed immediately. After an additional two hours, 0.5 g of sodium tetrahydridoborate was added. Two more additions of sodium tetrahydridoborate (0.5 g) were conducted within 1.5 hours, and the reaction mixture was further heated for 20 minutes. The total amount of sodium tetrahydridoborate added to the reaction mixture was 2.5 g, and the reaction was heated at 95° C. for 5 hours and 20 min. The reaction mixture was quenched with 25 ml of water and extracted with ethyl acetate (25 ml). The ethyl acetate layer was collected, dried over sodium carbonate, filtered through a short column of silica gel and washed with ethyl acetate. GC analysis was conducted and the efficiency of dichlorination was higher than in the case of one-time addition of sodium tetrahydridoborate.

EXAMPLE 19

The reducing agent was prepared as in Example 12.

(a) Reduction of PCB at 25° C.

A 20 ml vial equipped with a magnetic stir bar was charged with Aroclor 1248 (12.8 mg) and the ex situ prepared reducing agent (10 ml, 10.0 mmol). Reduction proceeded slowly at 25° C.

(b) Reduction of Tetrachloroethylene

A flask equipped with a magnetic stir bar and 30 ml of the ex situ prepared reducing reagent (30 mmol) was charged with tetrachloroethylene (0.452 mg, 3.0 mmol), 1-chlorooctane (0.441 g), and nonane (0.44 g). The reaction mixture was held at 25° C. for 40 hours, after which time analysis showed no tetrachloroethylene and only a small amount of chlorooctane remaining.

(c) Reduction of 1,2,3-Trichloropropane

A flask equipped with a magnetic stir bar and 1,2,3-trichloropropane-contaminated sand (20 g sand; 0.5 g trichloropropane and 0.67 g decane as an internal analysis standard) and the ex situ prepared reducing reagent (30 ml; 30 mmol). The mixture was heated at 52° C. for 3 hours; more than 95% 1,2,3-trichloropropane was reduced.

(d) Reduction of 1,2,4,5-Tetrachlorobenzene

A mixture of the ex situ prepared reducing reagent (40 ml; 64 mmol) and 1,2,4,5-tetrachlorobenzene (4.0 mmol) was held at 25° C. for two weeks. More than 70% of the tetrachlorobenzene was reduced.

EXAMPLE 20

A flask equipped with a magnetic stir bar was charged with bis($\eta^5$-cyclopentadienyl)titanium dichloride (55 mg, 0.22 mmol), sodium tetrahydridoborate (1230 mg, 32.5 mmol), 1,2,4,5-tetrachlorobenzene (0.449 g, 2.1 mmol), dimethylformamide (20.0 ml) and water (0.1 ml, corresponding to 1% water in the reaction mixture). The reaction was heated at 85° C. with the rate of reduction being shown in the following table.

| | Time (Hours) | Mole Fraction $C_4Cl_4$ |
|---|---|---|
| | 0% Water | |
| 1 | 0.250 | 0.990 |
| 2 | 0.500 | 0.990 |
| 3 | 0.750 | 0.970 |
| 4 | 1.000 | 0.900 |
| 5 | 1.250 | 0.600 |
| 6 | 1.300 | 0.001 |
| | 1% Water | |
| 1 | 4.000 | 0.940 |
| 2 | 8.000 | 0.890 |
| 3 | 12.000 | 0.830 |
| 4 | 16.000 | 0.050 |
| | 2% Water | |
| 1 | 12.500 | 0.900 |
| 2 | 14.000 | 0.860 |
| 3 | 16.000 | 0.820 |
| 4 | 18.000 | 0.780 |
| 5 | 20.000 | 0.020 |
| | 5% Water | |
| 1 | 14.000 | 0.920 |
| 2 | 18.000 | 0.890 |
| 3 | 22.000 | 0.860 |
| 4 | 26.000 | 0.820 |
| 5 | 30.000 | 0.770 |
| 6 | 34.000 | 0.090 |

What is claimed is:

1. A method of reducing chlorine content in a polychlorinated aromatic hydrocarbon in the absence of air and moisture which comprises bringing the polychlorinated aromatic hydrocarbon into contact with a dechlorination reagent, said reagent comprising:

(i) at least one complex of a transition metal of Group 4 or 5 with a multidentate or unidentate organic or inorganic ligand or a mixture thereof, and (ii) a reducing agent operable in the presence of said complex to reductively eliminate chlorine from said polychlorinated aromatic hydrocarbon.

2. The method of claim 1 in which the ligands of said ligand or mixture thereof are selected from the group consisting of benzoates, chlorides, metallocenes, salens, porphyrins, tris(pyrazolyl)borates, poly(alkylamino)s, and poly(thioalkyl)s.

3. The method of claim 1 in which the reducing agent is a hydridoborate or polyhydridoborate.

4. The method of claim 3 in which the reducing agent is an alkali metal, a metal chelate thereof, or ammonium salt of a polyhydrido compound selected from the group consisting of tetrahydridoborate, thiocyanatotrihydridoborate, cyanotrihydridoborate, acyloxytrihydridoborate, octahydridotrihydridoborate, trialkylhydridoborate, acetanilidotrihydridoborate, and trialkoxyhydridoborate.

5. The method of claim 4 in which the complex is bis-($\eta^5$-cyclopentadientyl)titanium dichloride and the reducing agent is sodium tetrahydridoborate.

6. The method of claim 5 in which the polychlorinated aromatic hydrocarbon is a mixture of polychlorinated biphenyls.

7. A method of reducing chlorine content in a chlorinated aliphatic hydrocarbon in the absence of air and moisture which comprises bringing the chlorinated hydrocarbon into contact with a dechlorination reagent, said reagent comprising:

(i) at least one complex of a transition metal of Group 4 or 5 with a multidentate or unidentate organic or inorganic ligand or mixture thereof, and (ii) a reducing agent operable in the presence of said complex to reductively eliminate chlorine from said chlorinated aliphatic hydrocarbon.

* * * * *